United States Patent [19]

Steiner et al.

[11] Patent Number: 4,665,186
[45] Date of Patent: May 12, 1987

[54] 2,2,4,4-TETRASUBSTITUTED 4-FORMYLBUTYRONITRILE INTERMEDIATES FOR THE PRODUCTION OF TRISUBSTITUTED PYRIDINES

[75] Inventors: Eginhard Steiner, Füllinsdorf; Pierre Martin, Rheinfelden, both of Switzerland

[73] Assignee: Ciba-Geigy Corporation, Ardsley, N.Y.

[21] Appl. No.: 846,243

[22] Filed: Mar. 31, 1986

Related U.S. Application Data

[60] Continuation-in-part of Ser. No. 511,829, Jul. 8, 1983, abandoned, which is a division of Ser. No. 293,804, Aug. 17, 1981, abandoned.

[30] Foreign Application Priority Data

Aug. 27, 1980 [CH] Switzerland .......................... 6447/80
Jun. 11, 1981 [CH] Switzerland .......................... 3834/81

[51] Int. Cl.[4] ........................................... C07D 213/09
[52] U.S. Cl. ..................................... 546/250; 558/440
[58] Field of Search ..................... 260/465.7; 558/440; 546/250

[56] References Cited

U.S. PATENT DOCUMENTS 3,132,173  5/1964  Gerber et al. ..................... 260/465.1
4,245,098  1/1981  Steiner et al. ....................... 546/250
4,435,573  3/1984  Lysenko et al. .................... 546/250
4,468,354  8/1984  Lysenko et al. ................. 546/250 X

OTHER PUBLICATIONS

Hackh's Chemical Dictionary, 4th ed., (edited by Julius Grant), 1969, p. 687; McGraw-Hill Book Co., N.Y., London.
Steiner, et al.; Helv. Chim. Acta., 65, (1982), pp. 983-985.

Primary Examiner—Joseph Paul Brust
Attorney, Agent, or Firm—Edward McC. Roberts; Bruce M. Collins

[57] ABSTRACT 2,2,4,4-Tetrasubstituted-4-formylbutyronitriles are intermediates for the preparation of the known 2-chloro-3,5-dimethylpyridine and 2,5-dichloro-3-methylpyridine which in turn are suitable for the production of different compounds, in particular insecticides and herbicides.

4 Claims, No Drawings

2,2,4,4-TETRASUBSTITUTED 4-FORMYLBUTYRONITRILE INTERMEDIATES FOR THE PRODUCTION OF TRISUBSTITUTED PYRIDINES

CROSS REFERENCE

This is a continuation-in-part of Ser. No. 511,829 filed July 8, 1983, now abandoned, which in turn is a division of Ser. No. 293,804 filed Aug. 17, 1981, now abandoned.

DETAILED DESCRIPTION

The present invention relates novel intermediates useful in the production of trisubstituted pyridines.

It has been found that trisubstituted pyridines of the formula

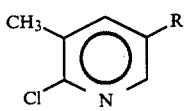
I wherein R is chloro or methyl can be obtained in a simple, economical and environmentally safe manner, and in good yield, from readily obtainable cheap starting materials by cyclizing the novel tetrasubstituted butyronitrile of the formula:

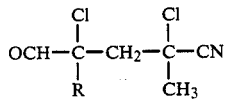
II wherein R is chloro or methyl.

The compounds of Formula II can be prepared by the addition of methacrylonitrile and either trichloroacetaldehyde (R=Cl) or or 2,2-dichloropropionaldehyde (R=CH$_3$). This reaction can be carried out in an open or closed system, preferably in the temperature range of from 70° to 160° C. It is preferred to carry out the reaction in a closed system under a pressure corresponding to the reaction temperature; e.g., in the range of from 1 to 30 bars.

Suitable catalysts for the addition reaction are metals of the main group VIII and of the subgroups VIa, VIIa, Ib and IIb of the periodic system, which catalysts are exemplified in greater detail in our U.S. Pat. No. 4,469,896, the disclosure of which is incorporated herein by reference.

Preferred catalysts are iron(II) and iron(III) salts and complexes, in particular iron(II) and iron(III) chloride, as well as iron powder; ruthenium(III) chloride, ruthenium(II) dichloro-tris-triphenylphosphine, copper powder, copper bronze, copper(I) and copper(II) salts and complexes such as copper(I) chloride, copper(II) chloride, copper(I) bromide, copper(II) bromide; copper(II) acetate, copper(II) acetylacetonate, copper(II) benzoylacetonate, copper(II) sulfate, copper(II) nitrate, copper(I) cyanide and copper(I) iodide. Most preferred catalysts are copper powder, copper bronze, copper(I) and copper(II) chloride or bromide and copper(I) iodide, as well as mixtures thereof.

The catalysts are generally used in amounts of about 0.01 to 10 mol.%, preferably 0.1 to 5 mol.%, based on the amount of aldehyde present.

The addition of aldehydes to methacrylonitrile is conveniently carried out in the presence of an inert organic solvent. Suitable solvents are those in which the catalysts are sufficiently soluble, or which are able to form complexes with the catalysts, but which are inert to the reactants. Representative examples of suitable solvents are disclosed in the above-noted U.S. Pat. No. 4,469,896.

Preferred solvents for the addition reactions are alkanecarbonitriles containing 2 to 5 carbon atoms and 3-alkoxypropionitriles containing 1 to 2 carbon atoms in the alkoxy moiety, in particular acetonitrile, butyronitrile, acrylonitrile and 3-methoxypropionitrile, or the methacrylonitrile used as reactant.

The cyclization of the compounds of Formula II can be carried out in an open or closed system in the temperature range from about 0° to 220° C., preferably from about 80° to 200° C. It is preferred to carry out the cyclization in an open system. Where the cyclization is carried out in an open system, it is advantageous to conduct this reaction in the presence of hydrogen chloride, or in the presence of a substance which forms hydrogen chloride under the reaction conditions, such as phosgene, boron trichloride, aluminium chloride, a trialkylammonium chloride containing 1–4 carbon atoms in each of the alkyl moieties, phosphorous pentachloride, phosphoryl chloride or phosphorous trichloride. It is preferred to carry out the cyclization in the presence of hydrogen chloride. The reaction proceeds with the formation of the trisubstituted pyridine of Formula I and hypochloric acid.

It is preferred to carry out the cyclization in the liquid phase or in the gas phase, without the addition of a solvent, by merely heating the compounds of Formula II. However, the cyclization can also be carried out in the presence of an organic solvent. Examples of suitble organic solvents are disclosed in the above-noted U.S. Pat. No. 4,469,896.

Preferred solvents for the cyclization reaction are chloroform, methylene chloride, cyclic ethers and dialkyl ether containing 1 to 4 carbon atoms in each of the alkyl moieties, particularly dioxane and diethyl ether, as well as N,N-dialkylamides of lower aliphatic carboxylic acids, preferably N,N-dimethylformamide.

The trisubstituted pyridines of Formula I can be used in a manner known for the production of different compounds, especially insecticides and herbicides (see for example Swiss Pat. No. 622 170; European Patent Publications Nos. 00176 and 04414; European Patent Application 81810181; German Offenlegungsschrift Specification 2 812 649 and 2 748 636; South African Pat. No. 7 802 440; Japanese Patent Publications 5 4115-380, 5 5038-356, 5 5079-369 and 56-39069; and Belgian Pat. No. 862 325).

The present invention is illustrated in more detail by the following Examples.

EXAMPLE 1

(a) Preparation of 4-formyl-2-methyl-2,4,4-trichlorobutyronitrile 14.7 g of trichloroacetaldehyde, 13.5 g of methacrylonitrile, 0.3 g of copper powder (activated by the method described for copper bronze in Org. Synth. Coll., Vol. III, 339) and 30 ml of acetonitrile are heated in an enamel autoclave for 15 hours to 100° C. After the mixture has cooled, the solvent is distilled off at about 40°–50° C. in a water jet vacuum. The residue is taken up in 50 ml of diethyl ether and the precipitated copper sludge is removed by filtration. The diethyl ether is distilled off and the residue is rectified in a high vacuum. The fraction boiling at 76°-78° C./13 Pa is collected in a receiving flask, yielding 13.8 g of 4-formyl-2-methyl-2,4,4-trichlorobutyronitrile in the form of a colorless oil.

IR spectrum (liquid) in cm$^{-1}$: 2250 (CN), 1750 (CO).

$^1$H-NMR spectrum (60 MHz in CDCl$_3$) in ppm: 9.30 (s, 1H, —CHO); 3.22 (s, 2H, H$_2$ on C-3); 2.60 (s, 3H, —CH$_3$).

Elemental analysis for C$_6$H$_6$Cl$_3$NO (mol. wt. 214.48): calculated: C 33.60% H 2.82% N 6.53% Cl 49.59%. found: C 34.1% H 3.1% N 6.8% Cl 48.6%.

(b) Preparation of 2,5-dichloro-3-methylpyridine 21.4 g of the 4-formyl-2-methyl-2,4,4-trichlorobutyronitrile obtained in 1) are heated for 4 to 5 hours to 145° C. while introducing a weak stream of dry HCl gas. After it has cooled, the dark melt is subject to steam distillation, affording 9.9 g of 2,5-dichloro-3-methylpyridine in the form of colorless crystals (recrystallized from CH$_3$OH/H$_2$O in the volume ratio of 4:1).

$^1$H-NMR spectrum (60 MHz in CDCl$_3$) in ppm: 8.15 (d, 1H, H and C-6); 7.50 (d, 1H, H on C-4); 2.40 (s, 3H, —CH$_3$).

Elemental analysis for C$_6$H$_5$Cl$_2$N (mol. wt. 162.02): calculated: C 44.48% H 3.11% N 8.65% Cl 43.77%. found: C 44.4% H 2.9% N 7.9% Cl 53.8%.

EXAMPLE 2

(a) Preparation of 4-formyl-2,4-dimethyl-2,4-dichlorobutyronitrile 12.7 g of 2,2-dichloropropionaldehyde, 13.5 g of methacrylonitrile, 0.5 g of copper(I) chloride and 40 ml of acetonitrile are heated in a tantalum autoclave for 1 hour to 130° C. and then for 2 hours to 150° C. The solvent and excess methacrylonitrile are distilled off in a water jet vacuum and the residue is taken up in 50 ml of diethyl ether and the ethereal solution is filtered. The diethyl ether is distilled off in vacuo and the residue is rectified in a high vacuum. The fraction boiling at 76°-77° C./13 Pa is collected in a received. Yield: 10.8 g of 4-formyl-2,4-dimethyl-2,4-dichlorobutyronitrile in the form of a light brown oil.

IR spectrum (liquid) in cm$^{-1}$: 2250 (CN), 1750 (CO).

$^1$H-NMR spectrum (60 MHz in CDCl$_3$) in ppm: (mixture of diastereoisomers in the ratio 1:1) 9.71 and 9.53 respectively (s, 1H, —CHO); 2.96 (s, 4H, 2x—CH$_2$); 2.14 (s, 6H, 2x—CH$_3$); 2.02 (s, 3H, —CH$_3$); 1.93 (s, 3H, —CH$_3$).

Elemental analysis for C$_7$H$_9$Cl$_2$NO (mol. wt. 194.06): calculated: C 43.22% H 4.67% N 7.21% C 36.53%. found: C 43.6% H 4.6% N 7.3% Cl 35.9%.

(b) Preparation of 2-chloro-3,5-dimethylpyridine 19.4 g of the 4-formyl-2,4-dimethyl-2,4-dichlorobutyronitrile obtained in Example 2a) are heated for 4 hours to 160°-170° while introducing a weak stream of dry HCl gas. After it has cooled, the dark melt is subjected to steam distillation. The distillate is extracted with diethyl ether and the extract is dried and evaporated to dryness in vacuo. The residual light brown oil is distilled, affording 7.36 g of 2-chloro-3,5-dimethylpyridine in the form of a light brown oil which boils at 110° C./2500 Pa.

$^1$H-NMR spectrum (60 MHz in CDCl$_3$) in ppm: 8.0 (d, 1H, H on c-6); 7.31 (d, 1H, H on C-4, J$_{6-4}$=2.0 Hz); 2.34 (s, 3H, —CH$_3$); 2.28 (s, 3H, —CH$_3$).

Elemental analysis for C$_7$H$_8$ClN (mol. wt. 141.60): calculated: C 59.38% H 5.65% N 9.83% Cl 25.04%. found: C 59.1% H 5.9% N 9.7% Cl 25.3%.

What is claimed is:

1. A tetrasubstituted 4-formylbutyronitrile of the formula

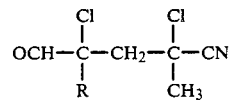

wherein R is chloro or methyl.

2. The compound according to claim 1 wherein R is chloro.

3. The compound according to claim 1 wherein R is methyl.

4. A process which comprises cyclizing a tetrasubstituted butyronitrile of the formula:

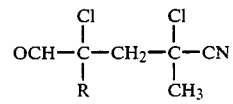

wherein R is chloro or methyl in the presence of a copper catalyst and at a temperature of from 70° to 160° C. to yield a trisubstituted pyridine of the formula:

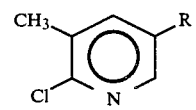

wherein R is as defined above.

* * * * *